US006556940B1

(12) United States Patent
Tretiakov et al.

(10) Patent No.: US 6,556,940 B1

(45) Date of Patent: Apr. 29, 2003

(54) RAPID HEAT BLOCK THERMOCYCLER

(75) Inventors: Alexandre Tretiakov, Jena (DE); Hans-Peter Saluz, Oberbodnitz (DE)

(73) Assignee: Analytik Jena AG, Jena (DE)

( * ) Notice: Subject to any disclaimer, the term of this patent is extended or adjusted under 35 U.S.C. 154(b) by 0 days.

(21) Appl. No.: 09/719,125

(22) PCT Filed: Apr. 5, 2000

(86) PCT No.: PCT/EP00/03224

§ 371 (c)(1), (2), (4) Date: Dec. 7, 2000

(87) PCT Pub. No.: WO00/61797

PCT Pub. Date: Oct. 19, 2000

(30) Foreign Application Priority Data

Apr. 8, 1999 (EP) ............................................ 99106900

(51) Int. Cl.[7] ............................ G01K 5/00; C12M 1/00

(52) U.S. Cl. .................... 702/130; 702/132; 435/286.1; 435/287.2

(58) Field of Search ................................ 702/130, 132, 702/136, 170, 97–99; 435/286.1, 286.6, 287.2, 288.1; 422/99, 104, 600–601

(56) References Cited

U.S. PATENT DOCUMENTS

| | | | | | |
|---|---|---|---|---|---|
| 5,455,175 | A | | 10/1995 | Wittwer et al. | |
| 5,475,610 | A | * | 12/1995 | Atwood et al. | 700/269 |
| 5,496,517 | A | | 3/1996 | Pfost et al. | |
| 5,508,197 | A | | 4/1996 | Hansen et al. | |
| 5,674,742 | A | | 10/1997 | Northrup et al. | |
| 5,710,381 | A | | 1/1998 | Atwood et al. | |
| 5,716,842 | A | | 2/1998 | Baier et al. | |
| 5,721,136 | A | * | 2/1998 | Finney et al. | 435/287.2 |
| 5,802,816 | A | | 9/1998 | Dietzel | |
| 6,261,431 | B1 | * | 7/2001 | Mathies et al. | 435/286.1 |

FOREIGN PATENT DOCUMENTS

| | | |
|---|---|---|
| DE | 4022792 | 2/1992 |
| DE | 19739119 | 3/1999 |
| WO | WO 98/43740 | 10/1998 |
| WO | WO 00/25920 | 5/2000 |

OTHER PUBLICATIONS

Analytical Biochemistry 186, 328–331 (1990) "Minimizing the Time Required for DNA Amplification by Efficient Heat Transfer to Small Samples" by Carl T. Wittwer et al.

Anal. Chem. 1998, 70, 2997–3002, "Capillary Tube Resistive Thermal Cycling" by Neal A. Friedman, et al..

The 7$^{th}$ International Conference on Solid–State Sensors and Actuators, 924–926, "DNA Amplification with Microfabricated Reaction Chamber" by M. Allen Northrup et al.

(List continued on next page.)

*Primary Examiner*—Bryan Bui

(74) *Attorney, Agent, or Firm*—Jordan and Hamburg LLP

(57) ABSTRACT

A heat block thermocycler to perform rapid PCR in multiple small-volume samples (1–20 $\mu$l) employing, low profile, low thermal mass sample block the temperature of which can be rapidly and accurately modulated by a single thermoelectric pump (thermoelectric module). An array of spaced-apart sample wells is formed in the top surface of the block. The samples are placed into the wells of ultrathin-walled (20–40 $\mu$m) multiwell plate and located into the sample block. The heated lid tightly seals the individual wells by pressing the sealing film to the top surface of the multiwell plate. Air pressure arising inside the tightly sealed wells at elevated temperatures deforms the elastic walls of the wells of the ultrathin-walled plate and brings them into close thermal contact with the sample block. A gasket thermally isolates the sample block from the heated lid. The PCR reactions (30 cycles) can be performed in 10–30 minutes.

21 Claims, 3 Drawing Sheets

OTHER PUBLICATIONS

Nucleic Acids Research, 1997, vol. 25, No. 15, "Optimization of the performance of the polymerase chain reaction in silicon–based microstructures" by Theresa B. Taylor et al..

Science, vol. 280, May 15, 1998, 1046–1048, "Chemical Amplification: Continuous–Flow PCR on a Chip" by Martin U. Kopp et al..

Product Application Focus, vol. 10, No. 1, (1991) 102–112, "A High–Performance System for Automation of the Polymerase Chain Reaction" by Haff et al.

"Rapid Thermal Cycling and PCR Kinetics" Carl T. Wittwer and Mark G. Hermann pp. 211–228, copyright 1999.

Products and Applications for the Laboratory eppendorf p143, 2002.

T Robot Thermocyler Whatman Biometra pp. 1–4, Jul. 2001.

Innovative PCR Plastics, Robbins pp. 1–10, copyright 1998.

PCR Instruments and Consumables 3pgs.

* cited by examiner a)

RAPID HEAT BLOCK THERMOCYCLER

BACKGROUND OF THE INVENTION

The invention relates to thermocyclers for an automatic performance of polymerase chain reaction (PCR), particularly to rapid thermocyclers. More specifically, it relates to rapid heat block thermocyclers for parallel processing of multiple small-volume samples. The present invention is especially useful for rapid, high-throughput, inexpensive and convenient PCR-based DNA-diagnostic assays.

Since it's first published account in 1985 polymerase chain reaction has been transformed into myriad array of methods and diagnostic assays. Temperature cycling of samples is the central moment in PCR. In recent years various rapid thermocyclers have been developed to address the slow processing speed and high sample volumes of conventional heat block thermocyclers. These rapid thermocyclers can be divided into two broad classes:

1. Capillary thermocyclers hold the samples within a glass capillary and supply heat convectively or conductively to the exterior of the capillary. For the description see Wittwer, C. T., et al., Anal.Biochem. 186: p328–331 (1990); Friedman, N. A., Meldrum, D. R. Anal. Chem., 70: 2997–3002 (1998) and U.S. Pat. No. 5,455,175.
2. Microfabricated thermocyclers are thermocyclers constructed of microfabricated components; these are generally etched structures in glass or silicon with heat supplied by integral resistive heating and rejected passively (or actively) to ambient by the structure. However, other schemes of thermocycling, as continuous flow thermocycling of samples are also used. For the description see Northrup, M. A., et al., Transducers 1993: 924–926 (1993); Taylor, T. B., et al, Nucleic Acid Res., 25: pp 3164–3168 (1997); Kopp, M. U. et al., Science, 280: 1046–1048 (1998); U.S. Pat. No. 5,674,742; U.S. Pat. No. 5,716,842.

Both classes of rapid thermocyclers employ the increased surface-to-volume ratio of the reactors to increase the rate of-heat transfer to small samples (1–20 μl). Total DNA amplification time is reduced to 10–30 minutes. Conventional heat block thermocyclers usually take 1–3 hours to complete temperature cycling of 20–100 μl samples. However, with these benefits also several disadvantages appear. Increased surface area between reagents and reactors causes a loss of enzyme activity. Furthermore, DNA can also be irreversibly adsorbed onto silica surface of the reactors, especially in the presence of magnesium ions and detergents that are the standard components of a PCR mixture. Therefore, PCR in glass-silicon reactors requires the addition of carrier protein (e.g. bovine serum albumin) and a rigorous optimization of the composition of the reaction mixture.

Another disadvantage of these reactors is the very complicated way of loading and recovering the samples. In addition, standard pipetting equipment is usually not compatible with such reactors. These inconvenient and cumbersome procedures are also time-consuming and labor-sensitive, thus limiting the throughput of the thermocyclers. Finally, although the reagents costs drop with a volume reduction to 1–10 μl, the final costs are relatively high due to a high cost of capillary and, especially, microfabricated reactors.

Therefore, it is surprising that only little research has been conducted to improve the basic performance in sample size and speed of the widely used, conventional heat block thermocycling of samples contained in plastic tubes or multiwell plates. One known improvement of heat block temperature cycling of samples contained in plastic tubes has been described by Half et al. (Biotechniques, 10, 106–112, [1991] and U.S. Pat. No. 5,475,610). They describe a special PCR reaction-compatible one-piece plastic, i.e. polypropylene, microcentrifuge tube, i.e. a thin-walled PCR tube. The tube has a cylindrically shaped upper wall section, a relatively thin (i.e. approximately 0.3 mm) conically- shaped lower wall section and a dome-shaped bottom. The samples as small as 20 μl are placed into the tubes, the tubes are closed by deformable, gas-tight caps and positioned into similarly shaped conical wells machined in the body of the heat block. The heated cover compresses each cap and forces each tube down firmly into its own well. The heated platen (i.e. heated lid) serves several goals by supplying the appropriate pressure to the caps of the tubes: it maintains the conically shaped walls in close thermal contact with the body of the block; it prevents the opening of the caps by increased air pressure arising in the tubes at elevated temperatures. In addition, it maintains the parts of the tubes that project above the top surface of the block at 95°–100° C. in order to prevent water condensation and sample loss in the course of thermocycling. This made it possible to exclude the placing of mineral oil or glycerol into the wells of the block in order to improve the heat transfer to the tubes and the overlaying of the samples by mineral oil that prevented evaporation but also served as added thermal mass. In addition, the PCR tubes can be put in a two-piece holder (U.S. Pat. No. 5,710,381) of an 8×12, 96-well microplate format, which can be used to support the high sample throughput needs with any number between 1 and 96 individual reaction tubes. When compared to conventional microcentrifuge tubes the use of thin-walled 0.2-ml PCR tubes made it possible to reduce the reaction time from 6–10 hours to 2–4 hours or less. At the same time it was also shown in DE 4022792 that the use of thin-walled polycarbonate microplates allows to reduce the reaction time to less than 4 hours. A recent improvement concerning the ramping rate (i.e. 3–4° C./second) of commercial thermoelectric (Peltier effect) heat block thermocyclers did not influence considerably the total reaction time. Moreover, it was concluded that a further increase in ramping rates will not be of a practical benefit due to the limited rate of heat transfer to the samples contained in thin-walled PCR tubes (see WO 98/43740).

SUMMARY OF THE INVENTION

The present invention bears some similarity to conventional heat block thermoelectric thermocyclers for performing PCR in plastic microplates (for example, see WO 98/43740 and DE 4022792). However, in contrast to conventional heat block thermocylers, it provides the means for performing PCR, i.e. 30 cycles, in 1–20 μl samples in 10–30 minutes. More specifically, it provides a rapid heat block thermocycler for convenient, high-throughput and inexpensive, oil-free temperature cycling of multiple small-volume samples.

Accordingly, the invention concerns a heat block thermocycler for subjecting a plurality of samples to rapid thermal cycling, the heat block thermocycler including:

- a unit for holding a plurality of samples having
  - an ultrathin-walled multiwell plate having an array of conically shaped wells and a low thermal mass sample block having an array of similarly shaped wells, wherein the height of the wells of the said multiwell plate is not more than the height of the wells of the said sample block, a unit for heating and cooling the sample block comprising at least one thermoelectric module, and a device for sealing the plurality of samples comprising a high-pressure heated lid.

BRIEF DESCRIPTION OF THE DRAWINGS

The invention is more specifically illustrated by the accompanying figures.

DETAILED DESCRIPTION OF THE INVENTION

A first aspect of the present invention concerns the use of low-profile, high sample density, ultrathin-walled multiwell plates (1) with considerably improved, i.e. 10-fold heat transfer to small, low thermal mass biological samples (i.e. 1–20 μl) (5) when compared to U.S. Pat. No. 5,475,610 and DE 4022792. Such plates can be produced, for example, out of thin thermoplastic films by means of various thermoforming methods.

Such thermoplastic films are, for example, polyolefin films, such as metallocene-catalyzed polyolefin films and/or copolymer films. Usually, the multiwell plate is vacuum formed out of cast, unoriented polypropylene film, polypropylene-polyethylene copolymer films or metallocene-catalyzed polypropylene films. The film is formed into a negative ("female") mould including a plurality of spaced-apart, conically shaped wells which are machined in the body of a mould in the shape of rectangular- or square-array. A thickness of the film for vacuum forming conically shaped wells is chosen according to the standard rule used for thermoforming, i.e. thickness of the film=well draw ration x thickness of the wall of the formed well.

For example, vacuum forming wells with a draw ratio of two and an average thickness of the walls of 30 microns results in a film thickness of 60 microns. The average optimum wall thickness was found to be 20–40 microns. The draw ratio is usually in the range of 2–3. The thickness of the film is usually 50–80 microns. The thickness of a small dome-shaped bottom is usually 10–15 microns. Using the heat-transfer equation as described in DE 4022792 it can be shown that the rate of heat transfer is increased approximately 10-fold when compared to U.S. Pat. No. 5,475,610 and DE 4022792.

Figure 1:
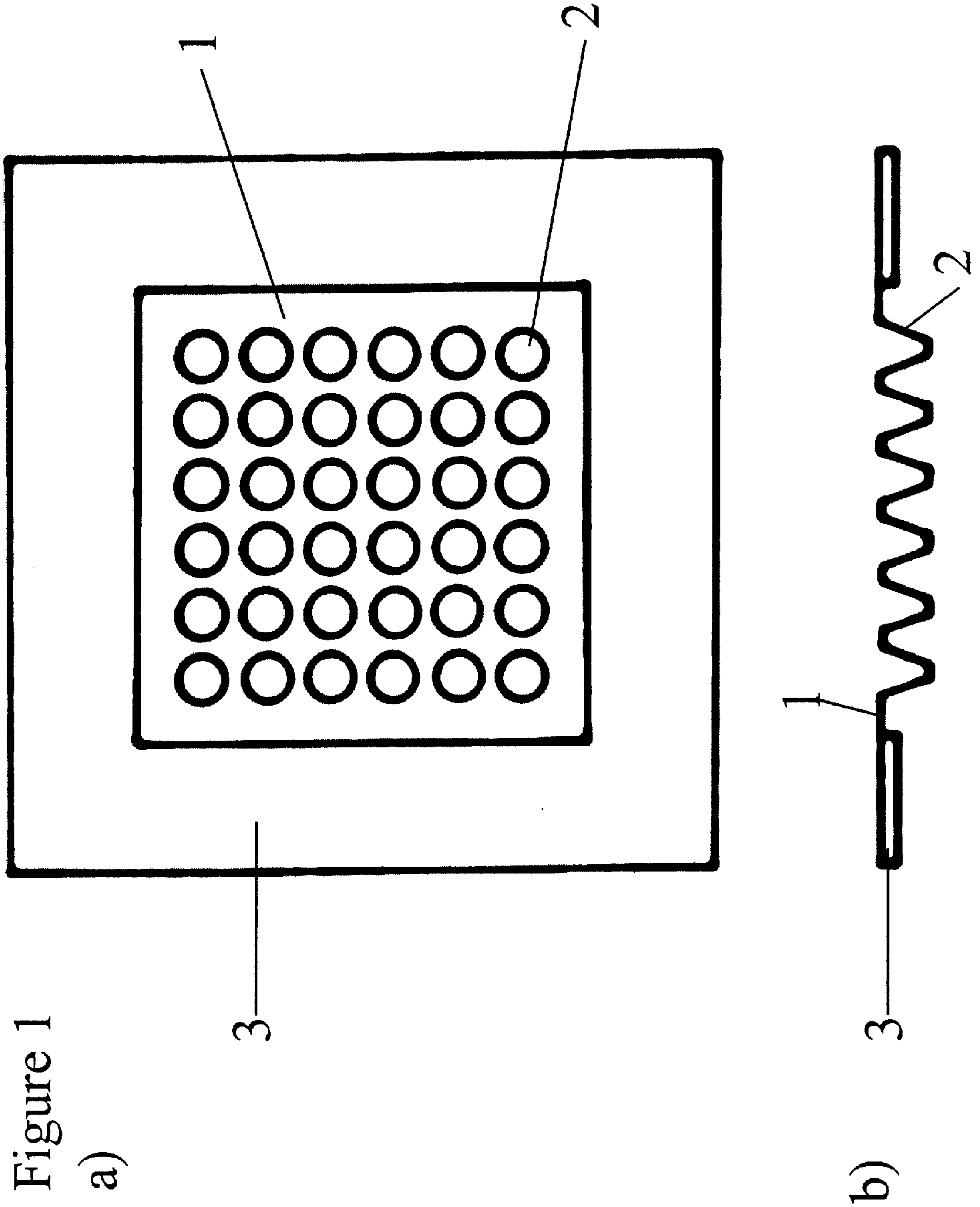
FIG. 1 illustrates a diagram of an ultrathin-walled microwell plate.

A volume of the wells is usually not more than 40 μl, preferably 16 μl or 25 μl, a height of the wells is not more than 3.8 mm, a diameter of the openings of the wells is not more than 4 mm and an inter-well spacing is usually industry standard, i.e. 4.5 mm. Usually the plates are vacuumformed in 36 well (6×6), 64 well (8×8) or 96 well (8×12) formats. As shown in FIG. 1, handling of the plate (1) containing multiple wells (2) is facilitated, by a rigid 0.5–1 mm thick plastic frame (3) which is heat bonded to the plate. However, for small format plates (36 and 64 well format) the plate including the frame is usually produced as one single piece during vacuum forming. The forming cycle is usually very short, i.e. 15–20 seconds. This allows even a manual production of approximately 1000 plates per person in 8 hours using one single mold vacuumforming device. The temperature of small samples (3–10 μl) contained in ultrathin-walled plates equilibrates with the temperature of the sample block (4) in 1–3 seconds. For comparison, it takes 15–20 seconds to equilibrate the temperature of, for example a 25-μl sample with the temperature of the sample block when the samples are contained in conventional thin-walled PCR tubes. The other principal advantage of the use of low-profile plates with relatively large openings of the wells (i.e. a diameter of 4 mm) for rapid temperature cycling of multiple samples is that small samples can be rapidly and accurately placed into the wells by means of conventional pipetting equipment. In this case no special skills are necessary when compared to the time consuming and labor-intense loading of capillaries or microreactors.

Figure 3:
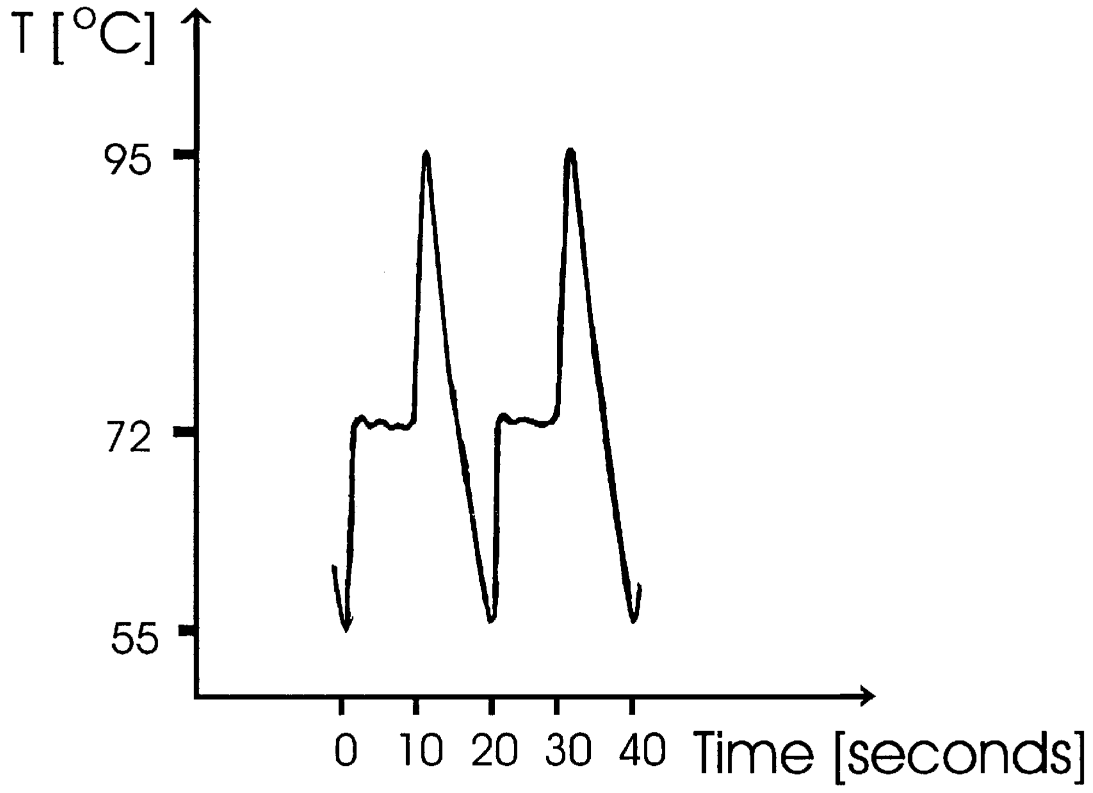
FIG. 3 illustrates a chart of temperature/time profile of the sample block.

The second aspect of the invention concerns the use of a low profile, low thermal capacity, for example the industry standard, silver sample blocks for holding the multiwell plates. A sample block (4) has a major top surface and a major bottom surface. An array of spaced-apart sample wells is formed in the top surface of the block. Usually the height of the block is not more than 4 mm. The thermal capacity of the blocks for holding 36–96-well plates is in the range of 4.5–12 Joules/K. The blocks supply an average thermal mass load of 0.5–0.6 Joules/K onto 1 $cm^2$ of the surface of thermoelectric module (12). Using industry standard high temperature, single-stage thermoelectric modules with maximum heat pumping power of 5–6 $Watts/cm^2$ of the surface area of the module the temperature of the sample blocks can be changed at the ramping rate of 5–10° C./second (FIG. 3). Usually, single industry standard thermoelectric modules, i.e. 30 mm×30 mm and 40 mm×40 mm, are used for temperature cycling using 36 and 64-well plates, respectively. A single thermoelectric module for heating and cooling has the advantage of an improved thermal contact between the module (12) and the sample block (4) and the module and an air-cooled heat sink (13) when compared to the use of multiple modules due to the height differences between the module. A thermocouple (14) with a response time not greater than 0.01 seconds is used for sensing the temperature of the sample block (4). The thermal mass of the copper heat sink (13) is usually in the range of 500–700 Joules/K. The relatively large thermal mass of the heat sink (13) compared to the thermal mass of the sample block (4) compensates the increased average heat load on the heat sink (13) during rapid thermocycling. A programmable controller (10) is used for a precise time and temperature control of the sample block (4).

Figure 2:
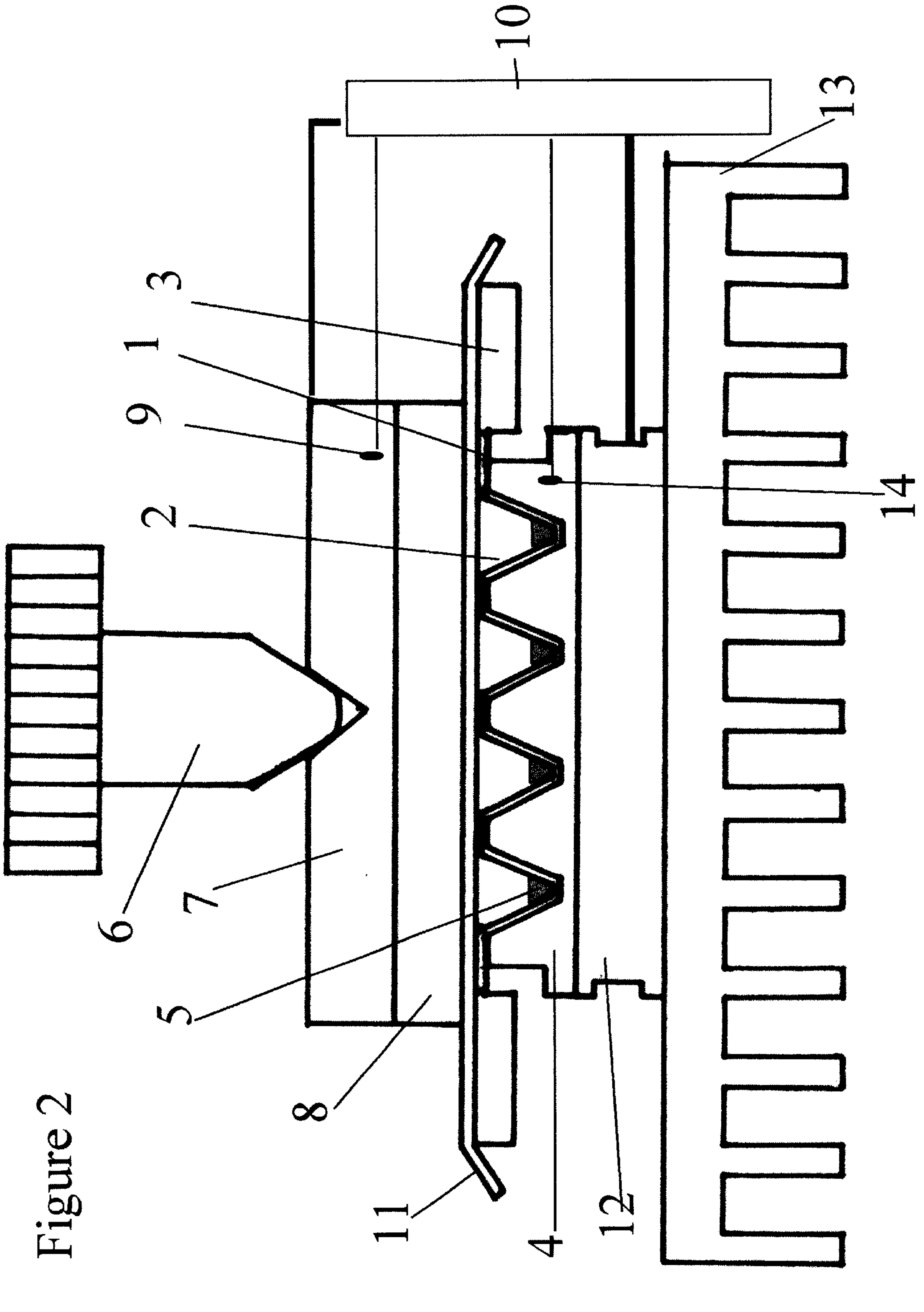
FIG. 2 illustrates a diagram of a rapid heat block thermocycler.

The third aspect of the invention is, that, in order to ensure an efficient and reproducible sealing of small samples (5) by using heated-lid technology, the height of the conically shaped wells (2) is not greater than the height of the similarly shaped wells machined in the body of the sample block (4) of the thermocycler. Due to the small surface of the bottom of the well of the plate, their is no need of a tight thermal contact between the bottom of the well and the body of the sample block. This is in contrast to DE 4022792, where a precise fitting of a large spherical bottom is needed for an efficient heat transfer. Thus, as shown in FIG. 2, the geometry of the wells enables the positioning of the entire multiwell plate (1) into the sample block (4). In this case the pressure caused by a screw mechanism (6) of the heated lid is actually directed to those parts of the multiwell plate which are supported by the top surface of the sample block (4) and not to the thin walls of the wells of the plate as it is the case for the PCR tubes or conventional PCR plates (see U.S. Pat. No. 5,475,610). This advantage makes it possible to increase the sealing pressure of the heated lid several fold (i.e. 5–10 fold) compared to the conventionally used pressure of 30–50 g per well without cracking the conically shaped walls. In contrary to the high pressure heated lid described in U.S. Pat. No. 5,508,197, the lid described here seals individual wells but not the edges of plate only. Therefore, even a single sample per multiwell plate can be amplified without sample loss. The tight thermal contact between the extremely thin walls of the wells and the body of the block (4) is achieved automatically by the increased air pressure arising in the sealed wells at elevated temperatures. The high pressure heated lid includes the screw mechanism (6), a heated metal plate (7) and a thermoinsulating gasket (8) isolating the sample block (4) from the metal plate (7). Conventionally, the metal plate (7) is heated by resistive heating, it's temperature is sensed by a thermistor (9) and controlled by the programmable controller (10). The gasket (8) is usually a 1.5–2 mm thick silicon-rubber gasket. It serves for a tight pressuring of a sealing film (11) to the top surface of the multiwell plate (1) and for the thermal isolation of the sample block (4 ) from the metal plate (7). The sealing film (11) is usually a 50 micron-thick polypropylene film. Surprisingly, by the above means of sealing the plates, samples of a volume of as few as, for example, 0.5 μl can be easily amplified without reducing the PCR efficiency.

For comparison, conventional, low-pressure heated lid (U.S. Pat. No. 5,475,610) and high pressure heated lid (U.S. Pat. No. 5,508,197) can be reliably used for oil-free temperature cycling of samples of a minimum volume of 15 μl–20 μl. However, it is clear that the use of ultrathin-walled microplates with elastic walls according to industry-standard formats and the method of sealing as described in FIG. 2 also improves the performance of conventional heat block thermocyclers in size and speed. To obtain a sufficient rigidity the plates can be formed, for example, out of reinforced plastic films by means of, for example, matched-die forming (stamping,-shaped rubber tool forming, hydroforming or other technologies. Furthermore, such plates can also be formed as two-piece parts, in which the frame (3) supports not only the edges of the plate but also individual wells (2). In this case, the height of the wells has to be measured from the bottom side of the frame. Such frames can be produced as skirted frames suitable for robotic applications.

Rapid heat block temperature cycler according to the invention (FIG. 2) was experimentally tested for the amplification of a 455-base pairs long fragment of human papilloma virus DNA. The sample volume was 3 μl. The temperature/time profile used for temperature cycling is shown in FIG. 3. The samples (i.e. standard PCR-mixtures without any carrier molecules) were transferred into the wells of the plate by means of conventional pipetting equipment. The plate was covered by sealing film (11), transferred into the heatblock of the thermocycler and tightly sealed by the heated lid as shown in FIG. 2. Upon sealing, a number of 30 PCR cycles was performed in 10 minutes using the temperature/time profile shown in FIG. 3. The heating rate was 10° C. per second, the cooling rate was 6° C. per second. The PCR product was analyzed by conventional agarose electrophoresis. The 455-base pairs long DNA fragment was amplified with a high specificity at the indicated ramping rates (supra).

Summarized, this invention has many advantages when compared to capillary or microfabricated rapid thermocyclers. Multiple small-volume samples can be easily loaded into the wells of ultrathin-walled multiwell plate by conventional pipetting equipment. Furthermore, they can be rapidly and efficiently sealed by using a high-pressure heated lid. Upon amplification the samples can be easily recovered for product analysis by electrophoresis or hybridization, thus allowing also high throughput amplification. Finally, standard PCR mixtures can be used for rapid temperature cycling without adding carriers, like BSA. Last but not least, the use of disposable, inexpensive, ultrathin-walled plates allows a great reduction of the total costs. It is obvious that the rapid heat block thermocycler according to the present invention can fabricated in various formats, i.e. multiblock thermocyclers, exchangable block thermocyclers, temperature gradient thermocyclers and others. Furthermore, it is obvious that it can be produced to perform the reactions in highsample density plates, such as 384-well plates or others.

The following example serves to illustrate the invention but should not be construed as a limitation thereof. Example: A heat block thermocycler for subjecting a plurality of samples to rapid thermal cycling according to the invention is depicted in FIG. 2, wherein 1) is a 36-well plate
2) is a 16 μl well
3) is a 0.5-mm thick plastic frame
4) is a 3 cm×3 cm sample block (with a thermal mass of 4,5 Joules/K)
5) is a 3-μl sample
6) is a screw mechanism of the heated lid
7) is a heated bronze plate (thickness: 5 mm)
8) is a thermoinsulating, 1.5 mm thick silicon-rubber gasket
9) is a termistor
10) is a programmable controller
11) is a 50 μm thick polypropylene sealing film
12) is a 57-watt thermoelectric module (3 cm×3 cm; Peltier module)
13) is an air cool copper heat sink (540 Joules/K)
14) is a thermocouple with a response time of approximately 0.01 second.

What we claim:

1. A heat block thermocycler for subjecting plurality of samples to rapid thermal cycling, the heat block thermocycler comprising:

a means for holding the plurality of samples including:

a deformable ultrathin-walled multiwell plate having an array of conically shaped wells with a wall thickness at a thickest part of the wells of not more than 50 μm; and a low profile, low thermal mass and low thermal capacity sample block having an array of similarly shaped wells, wherein a height of the wells of said deformable ultrathin-walled multiwell plate is not more than a height of said low profile, low thermal mass and low thermal capacity sample block;

a means for heating and cooling said low profile, low thermal mass and low thermal capacity sample block including at least one thermoelectric module; and a means for sealing the plurality of samples including a high pressure, moveable, heated lid.

2. A heat block thermocycler according to claim 1, wherein said deformable ultrathin-walled multiwell plate has a thinnest part in a bottom of each well.

3. A heat block thermocycler according to claim 1, wherein said deformable ultrathin-walled multiwell plate has a thickness at a thinnest part in the range of 15 μm to 20 μm.

4. A heat block thermocycler according to claim 3, wherein said low profile, low thermal mass and low thermal capacity sample block has a thermal capacity of not more than 6 watt seconds per ° C.

5. A heat block thermocycler according to claim 1, wherein each well of said deformable ultrathin-walled multiwell plate has a volume of not more than 40 μl.

6. A heat block thermocycler according to claim 1, wherein said low profile, low thermal mass and low thermal capacity sample block has a height of not more than 4 mm.

7. A heat block thermocycler according to claim 6, wherein said low profile, low thermal mass and low thermal capacity sample block has a thermal capacity of not more than 6 watt seconds per ° C.

8. A heat block thermocycler according to claim 7, wherein said low profile, low thermal mass and low thermal capacity sample block has a thermal mass of 4.5 Joules/K.

9. A heat block thermocycler according to claim 8, wherein said low profile, low thermal mass and low thermal capacity sample block is designed for biological samples of 1 μl–20 μl.

10. A heat block thermocycler according to claim 1, wherein said low profile, low thermal mass and low thermal capacity sample block has a thermal capacity of not more than 6 watt seconds per ° C.

11. A heat block thermocycler according to claim 10, wherein said low profile, low thermal mass and low thermal capacity sample block has a thermal mass of 4.5 Joules/K.

12. A heat block thermocycler according to claim 11, wherein said low profile, low thermal mass and low thermal capacity sample block is designed for biological samples of 1 μl–20 μl.

13. A heat block thermocycler according to claim 1, wherein said low profile, low thermal mass and low thermal capacity sample block has a thermal mass of 4.5 Joules/K.

14. A heat block thermocycler according to claim 13, wherein said low profile, low thermal mass and low thermal capacity sample block is designed for biological samples of 1 μl–20 μl.

15. A heat block thermocycler according to claim 1, wherein said low profile, low thermal mass and low thermal capacity sample block is designed for biological samples of 1 μl–20 μl.

16. A heat block thermocycler according to claim 1, wherein temperature of said low profile, low thermal mass and low thermal capacity sample block is rapidly and controllably increased and decreased at a rate of at least as great as 5° C. per second by a single thermoelectric module.

17. A heat block thermocycler according to claim 1, wherein force of the high pressure, moveable, heated lid is applied to said low profile, low thermal mass and low thermal capacity sample block.

18. A heat block thermocycler according to claim 1 wherein force of the high pressure, moveable, heated lid is applied to portions of said deformable ultrathin-walled multiwell plate lying between said wells of said low profile, low thermal mass and low thermal capacity sample block to seal the wells.

19. A heat block thermocycler according to claim 1, wherein force of the high pressure, moveable, heated lid is applied to portions of said deformable ultrathin-walled multiwell plate lying between said wells of said low profile, low thermal mass and low thermal capacity sample block to seal the wells and is not more than 100 Kg per total surface.

20. A heat block thermocycler according to claim 1, wherein the high pressure, moveable, heated lid includes an elastic insulating gasket.

21. A heat block thermocycler according to claim 1, wherein the high pressure, moveable, heated lid includes a silicon rubber gasket.

* * * * *